United States Patent [19]
Krause et al.

[11] Patent Number: 5,124,068
[45] Date of Patent: * Jun. 23, 1992

[54] PYRIMIDINES

[75] Inventors: Joachim Krause, Dieburg; Rudolf Eidenschink, Münster; Reinhard Hittich, Modautal; Bernhard Scheuble, Alsbach, all of Fed. Rep. of Germany

[73] Assignee: Merck Patent Gesellschaft Mit Beschrankter Haftung, Darmstadt, Fed. Rep. of Germany

[*] Notice: The portion of the term of this patent subsequent to Aug. 27, 2008 has been disclaimed.

[21] Appl. No.: 559,761

[22] Filed: Jul. 30, 1990

Related U.S. Application Data

[62] Division of Ser. No. 918,949, filed as PCT/EP85/00732, Dec. 20, 1985, Pat No. 5,043,093.

[30] Foreign Application Priority Data

Jan. 12, 1985 [DE] Fed. Rep. of Germany ....... 3500909

[51] Int. Cl.⁵ .................... C09K 19/34; C09K 19/54; C07D 239/02
[52] U.S. Cl. .................. 252/299.61; 252/299.5; 544/298
[58] Field of Search .............. 252/299.5, 299.61; 544/298

[56] References Cited

U.S. PATENT DOCUMENTS

| | | | |
|---|---|---|---|
| 4,393,121 | 7/1983 | Misaki et al. | 560/73 |
| 4,695,651 | 9/1987 | Higuchi et al. | 560/141 |
| 4,725,688 | 2/1988 | Taguchi et al. | 544/298 |
| 4,780,241 | 10/1988 | Furukawa et al. | 252/299.63 |
| 4,788,000 | 11/1988 | Ishii et al. | 252/299.61 |
| 4,808,333 | 2/1989 | Huynh-ba et al. | 252/299.66 |
| 4,812,258 | 3/1989 | Krause et al. | 252/299.61 |
| 4,844,597 | 7/1989 | Katagiri et al. | 350/350.5 |
| 4,886,619 | 12/1989 | Janulis | 252/299.1 |
| 5,043,093 | 8/1991 | Krause et al. | 252/299.61 |

FOREIGN PATENT DOCUMENTS 95892 12/1971 Fed. Rep. of Germany.

OTHER PUBLICATIONS

Titov, V. et al., "Synthesis and Mesomorphism of Aryl p-flouro alkyl (alkoxy) benzoates", Molecular Crystals Liquid Crystals, (1978) vol. 47, pp. 1–5.

Zaschke, Demus, Flüssige Kristalle in Tabellen, VEB Leipzig, Band 11, 1984.
Zaschke, Stolle, Z. Chem. 15, (1975), 11, S. 441–443.
H. Zaschke, Dissertation B, Universität Halle (Saale), 1977.

Primary Examiner—Robert L. Stoll
Assistant Examiner—C. Harris
Attorney, Agent, or Firm—Millen, White & Zelano

[57] ABSTRACT

Pyrimidines of the formula I

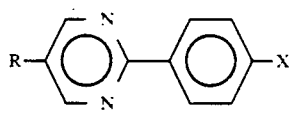

in which
R is an alkyl group of 1–15 C atoms in which in addition one or two nonadjacent $CH_2$ groups can be replaced by —O—, —CO—, —O—CO—, —CO—O—, —CHY— and/or —CH=CH—, or is H, F, Cl or CN,
X is —O—$CH_2$—$R^1$, —S—$R^2$, —NCS or —COO—A—$R^3$,
Y is halogen, CN or OH,
$R^1$ is an alkyl group of 1–15 C atoms, in which one or more nonadjacent $CH_2$ groups are replaced by —O—, —CO—, —O—CO—, —CHY— and/or by —CH=CH—,
$R^2$ is an alkyl group of 1–15 C atoms, in which in addition one or two nonadjacent $CH_2$ groups can be replaced by —O—, —CO—, —O—CO—, —CO—O—, —CHY— and/or —CH=CH—,
A is a trans-1,4-cyclohexylene groups which is unsubstituted or monosubstituted or disubstituted by F and/or Cl atoms and/or $CH_3$ groups and/or CN groups, or is a single bond, and
$R^3$ is an alkyl group of 1–15 C atoms, in which in addition one or two nonadjacent and, if A is a single bond, nonterminal $CH_2$ groups can be replaced by O atoms and/or —CH=CH— groups,
with the proviso that R is an alkyl group having 1–15 C atoms, in which in addition one or two nonadjacent $CH_2$ groups can be replaced by —O—, —O—CO—, —CO—O— and/or —CH=CH—, if X is —S—$R^2$, can be used as components of liquid-crystalline phases.

7 Claims, No Drawings

PYRIMIDINES

This is a division of application Ser. No. 06/918,949 filed as PCT/EP85/00732, Dec. 20, 1985, now U.S. Pat. No. 5,043,093.

The invention relates to compounds of the formula

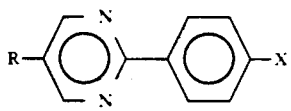

in which

R is an alkyl group of 1-15 C atoms in which in addition one or two nonadjacent $CH_2$ groups can be replaced by —O—, —CO—, —O—CO—, —CO—O—, —CHY-and/or —CH=CH—, or is H, F, Cl or CN, X is —O—$CH_2$—$R^1$, —S—$R^2$, —NCS or —COO—A—$R^3$, Y is halogen, CN or OH, $R^1$ is an alkyl group of 1-15 C atoms, in which one or more nonadjacent $CH_2$ groups are replaced by —O—, —CO—, —O—CO—, —CO—O—, —CHY— and/or by —CH=CH—, $R^2$ is an alkyl group of 1-15 C atoms, in which in addition one or two nonadjacent $CH_2$ groups can be replaced by —O—, —CO—, —O—CO—, —CO—O—, —CHY-and/or —CH=CH—, A is a trans-1,4-cyclohexylene group which is unsubstituted or monosubstituted or disubstituted by F and/or Cl atoms and/or CH3 groups and/or CN groups, or is a single bond, and $R^3$ is an alkyl group of 1-15 C atoms, in which in addition one or two nonadjacent and, if A is a single bond, nonterminal $CH_2$ groups can be replaced by 0 atoms and/or —CH=CH— groups, with the proviso that R is an alkyl group having 1-15 C atoms, in which in addition one or two nonadjacent $CH_2$ groups can be replaced by —O—, —O—CO—, —CO—O— and/or —CH=CH—, if X is —S—$R^2$.

For simplicity, hereinafter Cy is an optionally substituted 1,4-cyclohexylene group, Phe is a 1,4-phenylene group and Pyr is a pyrimidine-2,5-diyl group.

Similar compounds are known for example from Japanese Offenlegungsschrift 56-164,169. However, the three ring compounds specified there do not, unlike the present compounds, contain saturated rings (Cy).

The compounds of the formula I, like similar compounds, can be used as components of liquid-crystalline phases, in particular for displays which are based on the principle of the twisted cell (TN displays), the guest-host effect, the effect of the deformation of aligned phases or the effect of dynamic scattering.

The invention had for its object to find new stable liquid-crystalline or mesogenic compounds which are suitable for use as components of liquid-crystalline [sic] phases.

It was found that the compounds of the formula I are highly suitable for use as components of liquid-crystalline phases. In particular, with their aid it is possible to prepare stable liquid-crystalline phases for TN displays having high multiplexing rates.

The trinuclear compounds of the formula I thereby make possible the development of highly multiplexible mixtures of very small optical anisotropy, with which a twisted cell can be operated in particular in the first Gooch-Tarry transmission minimum. The result is consequently a very small dependence of the angle of observation on the contrast. The dinuclear compounds of the formula I have particularly favorable elastic constants and an excellent low-temperature stability. By providing the compounds of the formula I, in addition, the range of liquid-crystalline substances which are suitable from various application aspects for preparing nematic mixtures is, in general, quite appreciably widened.

The compounds of the formula I have a wide application area. Depending on the choice of substituents, these compounds can serve as base materials of which liquid-crystalline dielectrics are predominantly composed; however, it is also possible to add compounds of the formula I to liquid-crystalline base materials of other compound classes, for example in order to vary the dielectric and/or optical anisotropy of such a dielectric or in order to improve the elastic properties. The compounds of the formula I are further suitable for use as intermediates for preparing other substances which can be used as constituents of liquid-crystalline dielectrics. Some of the compounds of the formula I merely exhibit monotropic liquid-crystalline properties. However, such compounds are also highly suitable for use as constituents of liquid-crystalline dielectrics.

The compounds of the formula I are colorless in the pure state and form liquid-crystalline mesophases in a temperature range which is favorable for electro-optical use. They are very stable chemically, thermally and to light.

The invention thus provides the compounds of the formula I. The invention further provides the use of the compounds of the formula I as components of liquid-crystalline phases. The invention further provides liquid-crystalline phases containing at least one compound of the formula I and also liquid crystal display elements, in particular electro-optical display elements, which contain such phases.

Heretofore and hereinafter R, $R^1$, $R^2$, $R^3$, X, Y and A have the indicated meaning, unless otherwise stated.

The compounds of the formula I correspondingly encompass compounds of the partial formulae Ib to Ie (with two rings) and If (with three rings):

| | |
|---|---|
| R—Pyr—Phe—$OCH_2R^1$ | Ib |
| R—Pyr—Phe—NCS | Ic |
| R—Pyr—Phe—$SR^2$ | Id |
| R—Pyr—Phe—$COOR^3$ | Ie |
| R—Pyr—Phe—COO—Cy—$R^3$ | If |

In the compounds of the foregoing and the following formulae, R is preferably alkyl, and also alkoxy, oxaalkyl or CN (with the exception of Id).

The alkyl radicals in the groups R and/or $R^1$ and/or $R^2$ and/or $R^3$ can be straight-chain or branched. Preferably they are straight-chain, have 2, 3, 4, 5, 6, 7, 8, 9, 10, 11 or 12 C atoms and accordingly are preferably ethyl, propyl, butyl, pentyl, hexyl, heptyl, octyl, nonyl, decyl, undecyl or dodecyl, and also methyl, tridecyl, tetradecyl or pentadecyl.

When these radicals are alkyl radicals in which one ("alkoxy" or "oxaalkyl") or two ("alkoxyalkoxy" or "dioxaalkyl") $CH_2$ groups have been replaced by 0 atoms, they can be straight-chain or branched. Preferably they are straight-chain, have 2, 3, 4, 5, 6 or 7 C atoms and accordingly are preferably ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3-or 4-oxapentyl, 2-, 3-, 4- or 5-oxahexyl, 2-, 3-, 4-, 5-or 6-oxaheptyl, and also methoxy, octoxy, nonoxy, decoxy, 2-, 3-, 4-, 5-, 6- or 7-oxaoctyl, 2-, 3-, 4-, 5-, 6-, 7-or 8-oxanonyl, 2-, 3-, 4-, 5-, 6-, 7-, 8- or 9-oxadecyl, 1,3,-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formulae I and also of the foregoing and following partial formulae with branched wing groups can occasionally, on account of a higher solubility in the customary liquid-crystalline base materials, be of importance, but in particular as chiral dopants, if they are optically active. Branched groups of this kind generally contain not more than one chain branching. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentyoxy, 2-ethylhexoxy, 1-methylhexoxy, 1-methylheptoxy, 2-oxa-3-methylbutyl, 3-oxa-4-methylpentyl, 2-octyloxy.

Of the compounds of the formulae I and also of the foregoing and following partial formulae, preference is given to those in which at least one of the radicals contained therein has one of the indicated preferred meanings. Particularly preferred smaller groups of compounds are those of the formulae I1 to I14.

| | |
|---|---|
| Alkyl—Pyr—Phe—COO—Alkyl | I1 |
| Alkoxy—Pyr—Phe—COO—Alkyl | I2 |
| NC—Pyr—Phe—COO—Alkyl | I3 |
| Alkyl—Pyr—Phe—COO—Cy—Alkyl | I4 |
| Alkoxy—Pyr—Phe—COO—Cy—Alkyl | I5 |
| Alkyl—Pyr—Phe—COO—Cy—CN | I6 |
| Alkyl—Pyr—Phe—COO—Cy—Alkoxy | I7 |
| Oxaalkyl—Pyr—Phe—NCS | I8 |
| Alkyl—CH CH—CH₂CH₂—Pyr—Phe—NCS | I9 |
| Alkyl—Pyr—Phe—O—CH₂—O—Alkyl | I10 |
| Alkyl—Pyr—Phe—O—CH₂CH₂—O—Alkyl | I11 |
| Alkyl—Pyr—Phe—S—Alkyl | I12 |
| Alkyl—Pyr—Phe—NCS | I13 |
| Alkoxy—Pyr—Phe—NCS | I14 |

In the foregoing formulae I1 to I14, alkyl is preferably a straight-chain alkyl group having 2 to 10 C atoms and alkoxy a straight-chain alkoxy group having 2 to 12 C atoms. Particular preference is given to compounds of the formulae I1, I4 and I13, in particular I13.

In the foregoing formulae I1 to I14 Cy is preferably an unsubstituted trans-1,4-cyclohexylene group, and also preferably a monosubstituted 1,4-cyclohexylene group of the formula

in which
X¹ is F, Cl, CH₃ or CN, preferably CN.
X is preferably —O—CH₂—R¹, —S—R², —NCS or —COO—A—R³, particularly preferably —COO—A—R³ or —NCS.
R¹ is preferably in each case straight-chain alkoxy or oxaalkyl having in each case two to twelve C atoms.
R² is preferably straight-chain alkyl having 3 to 15, in particular 5 to 12, C atoms.
R³ is preferably straight-chain alkyl or alkoxy having 1 to 12, in particular 2 to 10, C atoms. When A is a single bond, R³ is preferably straight-chain or branched alkyl having 1 to 10 C atoms, preferably having 2 to 10 C atoms.
A is preferably a single bond or trans-1,4-cyclo-hexylene, particularly preferably a single bond.

Particular preference is given to compounds of the formula I and also of the foregoing partial formulae in which R is a straight-chain alkyl group having 1 to 10 C atoms.

The compounds of the formula I are prepared by methods known per se, as described in the literature (for example in standard works such as Houben-Weyl, Methoden der Organischen Chemie [Methods of Organic Chemistry], George-Thieme-Verlag, Stuttgart), specifically under reaction conditions which are known and suitable for the reactions mentioned. Therein it is also possible to use variants known per se which are not specified here in more detail.

The skilled worker can find appropriate synthetic methods in the prior art by routine methods.

The starting materials can, if desired, also be formed in situ, namely by not isolating them from the reaction mixture but immediately reacting them further to the compounds of the formula I.

In this way, the compounds of the formula Ie and If can be obtained by esterifying appropriate carboxylic acids (or their reactive derivatives) with alcohols (or their reactive derivatives).

Suitable reactive derivatives of the carboxylic acids mentioned are in particular the acid halides, in particular the chlorides and bromides, and also the anhydrides, azides or esters, in particular alkyl esters having 1–4 C atoms in the alkyl group.

Suitable reactive derivatives of the alcohols mentioned are in particular the corresponding metal alcoholates, preferably of an alkali metal such as Na or K.

The esterification is advantageously carried out in the presence of an inert solvent. Highly Suitable are in particular ethers such as diethyl ether, di-n-butyl ether, THF, dioxane or anisole, ketones such as acetone, butanone or cyclohexanone, amides such as DMF or hexamethylphosphoric triamide, hydrocarbons such as benzene, toluene or xylene, halohydrocarbons such as carbon tetrachloride or tetrachloroethylene and sulfoxides such as dimethyl sulfoxide or sulfolane. Water-immiscible solvents can at the same time be advantageously used for removing the water formed in the course of the esterification by azeotropic distillation. Occasionally it is also possible to use an excess of an organic base, for example pyridine, quinoline or triethylamine, as a solvent for the esterification. The esterification can also be carried out in the absence of a solvent, for example by simply heating the components in the presence of sodium acetate. The reaction temperature is customarily between $-50°$ and $+250°$, preferably between $-20°$ and $+80°$. At these temperatures, the esterification reactions are generally complete after 15 minutes to 48 hours.

In detail, the reaction conditions for the esterification largely depend on the nature of the starting materials used. For instance, a free carboxylic acid is generally reactive with a free alcohol or phenol in the presence of a strong acid, for example a mineral acid such as hydrochloric acid or sulfuric acid. A preferred way of carrying out the reaction is the reaction of an acid anhydride or, in particular, of an acid chloride with an alcohol, preferably in a basic medium, important bases being in particular alkali metal hydroxides such as sodium hydroxide or potassium hydroxide, alkali metal carbonates or hydrogencarbonates such as sodium carbonate, sodium hydrogencarbonate, potassium carbonate or potassium hydrogencarbonate, alkali metal acetates such as sodium acetate or potassium acetate, alkaline earth metal hydroxides such as calcium hydroxide or organic bases such as triethylamine, pyridine, lutidine, collidine or quinoline. A further preferred embodiment of the esterification comprises converting the alcohol or phenol first into the sodium or potassium alcoholate or phenolate, for example by treatment with ethanolic sodium hydroxide or potassium hydroxide solution, isolating this alcoholate or phenolate and suspending it together with sodium hydrogencarbonate or potassium carbonate with stirring in acetone or diethyl ether, and adding to this suspension a solution of the acid chloride or anhydride in diethyl ether, acetone or DMF, preferably at temperatures between $-25°$ and $+20°$.

Compounds of the formulae Ia, Ib and Id can be obtained for example by reacting 3-methoxyacrolein derivatives which are appropriately substituted in the 2-position with an acid addition salt of an appropriate amidine in the presence of a base (German Offenlegungsschrift 3,140,868).

The reaction of an acrolein derivative with an acid addition salt of an amidine is preferably carried out in water or an organic solvent, for example an alcohol such as methanol, ethanol, ethylene glycol and the like, in the presence of a base. Preferred solvents are methanol and ethanol. The addition salts can be salts of hydrochloric acid, hydrobromic acid, sulfuric acid, toluene-p-sulfonic acid and the like. However, preference is given to the use of the hydrochloride. Preferred bases are the alkali metal alcoholates, in particular sodium methylate and sodium ethylate. Temperature and pressure are not critical aspects in this reaction. It is preferable to use atmospheric pressure and a temperature between room temperature and reflux temperature, preferably room temperature.

Compounds of the formulae Ia, Ib and Id can further be obtained by reacting appropriately substituted malondialdehydes or their reactive derivatives with an acid addition salt of an appropriate amidine.

Eligible as suitable reactive derivatives of the malondialdehydes are primarily tetraalkyl acetals in which alkyl is lower alkyl having 1 to 5 carbon atoms, preferably methyl or ethyl. The reaction is preferably carried out in an organic solvent, such as, for example, dimethyl sulfoxide, dimethylformamide or hexamethylphosphoramide. Suitable addition salts of appropriate amidines are preferably the salts described above.

Temperature and pressure are not critical aspects in the reaction. It is preferable to use atmospheric pressure and temperatures between room temperature and 200°, preferably 100° to 180°.

Compounds of the formula Ib and compounds of the formulae Ia and Ib in which $R^1$ is an alkyl group in which at least one $CH_2$ group has been replaced by —O— are obtainable by etherifying appropriate hydroxy compounds, preferably appropriate phenols, the hydroxy compound being preferably first converted into a corresponding metal derivative, for example by treatment with NaOH, KOH, $Na_2CO_3$ or $K_2CO_3$ into the corresponding alkali metal alcoholate or alkali metal phenolate. This can then be reacted with the corresponding alkyl halide, alkyl sulfonate or dialkyl sulfonate, preferably in an inert solvent such as acetone, DMF or dimethyl sulfoxide or even an excess of aqueous or aqueous alcoholic NaOH or KOH at temperatures between about 20° and 100°.

Compounds of the formulae Ia and Ib in which $R^1$ is an alkyl group in which at least one $CH_2$ group has been replaced by —CO—O— or O—CO— can be obtained by esterification of appropriate carboxylic acids (or their derivatives capable of relation with alcohols (or their derivatives capable of relation, the reaction being particularly carried out as described above.

Compounds of the formula Ic can be obtained for example by reacting appropriate primary amines with thiophosgene under reaction conditions which are known and suitable for this reaction (Twitchett, Chem. Soc. Rev. 3, 209–230 (1974)). Compounds of the formula Ic are further obtainable by reacting appropriate primary amines with hydrogen sulfur, for example in pyridine in the presence of dicyclohexylcarbodiimide (Jochims and Seeliger, Angew. Chem. 79, 151 (1967)).

The amines used as starting materials can be prepared by methods known per se, for example by Hofmann degradation from the corresponding amides which are obtainable from known nitriles (German Patent 2,547,737).

The liquid-crystalline phases according to the invention consist of 2 to 25, preferably 3 to 15, components, including at least one compound of the formula I. The other constituents are preferably selected from the nematic or nematogenic substances, in particular the known substances, from the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenyldioxanes, cyclohexyldioxanes, phenyl- or cyclohexyl-1,3-dithianes, 1,2-bis-cyclohexylethanes, 1,2-bis-phenylethanes, 1-phenyl-2-cyclohexylethanes, optionally halogenated stilbenes, benzyl phenyl ethers, tolanes and substituted cinnamic acids.

The most important compounds which the suitable for use as constituents of such liquid-crystalline phases can be characterized by the formula II

R'—L—G—E—R"            II in which L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline.

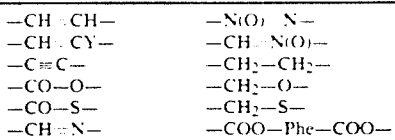

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —CN, and R' and R" are alkyl, alkoxy, alkanoyloxy or alkoxycarbonyloxy having up to 18, preferably up to 8, carbon atoms, or one of these radicals is also CN, NC, NO$_2$, CF$_3$, F, Cl or Br.

In most of these compounds, R' and R" are different from each other, one of these radicals usually being an alkyl or alkoxy group. However, other variants of the proposed substituents are likewise customary. Many such substances or even mixtures thereof are commercially available. All these substances can be prepared by methods described in the literature.

The phases according to the invention contain about 0.1 to 99, preferably 10 to 95, % of one or more compounds of the formula I. Preference is further given to dielectrics according to the invention containing 0.1 to 40, preferably 0.5 to 30, % of one or more compounds of the formula I.

The preparation of the dielectrics according to the invention is effected in conventional manner. In general the components are dissolved in one another, preferably at elevated temperature.

By means of suitable additives the liquid-crystalline dielectrics according to the invention can be modified in such a way that they can be used in all hitherto disclosed types of liquid crystal display elements.

Such additives are known to the skilled worker and are described in detail in the literature. It is possible to add for example conductive salts, for example ethyldimethyldodecylammonium 4-hexyloxybenzoate, tetrabutylammonium tetraphenylboronate or complex salts of crown ethers (cf. for example I. Haller et al., Mol. Cryst. Liq. Cryst. Volume 24, pages 249–258 (1973)) for improving the conductivity, dichroic dyes for preparing colored guest-host systems or substances for changing the dielectric anisotropy, the viscosity and/or the orientation of the nematic phases. Such substances are described for example in German Offenlegungsschriften 2,209,127, 2,240,864, 2,321,632, 2,338,281, 2,450,088, 2,637,430, 2,853,728 and 2,902,177.

The examples below are intended to illustrate the invention without limiting it. m.p. = melting point, c.p. = clear point. Heretofore and hereinafter percentages are by weight; all temperatures are given in degrees celsius. "Customary working up" means: adding water, extracting with methylene chloride, separating off, drying the organic phase, evaporating to dryness and purifying the product by crystallization and/or chromatography.

EXAMPLE 1

A mixture of 2.6 g of p-(5-n-propylpyrimidyl)benzoyl chloride, 25 ml of pyridine and 1.2 g of trans-4-methylcyclohexanol is stirred at 60° for 2 hours and, after cooling down, is worked up as customary. This gives trans-4-methylcyclohexyl p-(5-n-propylpyrimidyl)benzoate.

Prepared analogously:
trans-4-ethylcyclohexyl p-(5-propylpyrimidyl)-benzoate
trans-4-propylcyclohexyl p-(5-propylpyrimidyl)-benzoate
trans-4-butylcyclohexyl p-(5-propylpyrimidyl)-benzoate
trans-4-pentylcyclohexyl p-(5-propylpyrimidyl)-benzoate
trans-4-heptylcyclohexyl p-(5-propylpyrimidyl)-benzoate
trans-4-cyanocyclohexyl p-(5-propylpyrimidyl)-benzoate
trans-4-ethoxycyclohexyl p-(5-propylpyrimidyl)-benzoate
trans-4-butoxycyclohexyl p-(5-propylpyrimidyl)-benzoate
trans-4-hexoxycyclohexyl p-(5-propylpyrimidyl)-benzoate
trans-4-ethylcyclohexyl p-(5-butylpyrimidyl)-benzoate
trans-4-propylcyclohexyl p-(5-butylpyrimidyl)-benzoate
trans-4-butylcyclohexyl p-(5-butylpyrimidyl)-benzoate
trans-4-pentylcyclohexyl p-(5-butylpyrimidyl)-benzoate
trans-4-heptylcyclohexyl p-(5-butylpyrimidyl)-benzoate
trans-4-cyanocyclohexyl p-(5-butylpyrimidyl)-benzoate
trans-4-ethoxycyclohexyl p-(5-butylpyrimidyl)-benzoate
trans-4-butoxycyclohexyl p-(5-butylpyrimidyl)-benzoate
trans-4-hexoxycyclohexyl p-(5-butylpyrimidyl)-benzoate
trans-4-ethylcyclohexyl p-(5-pentylpyrimidyl)-benzoate
trans-4-propylcyclohexyl p-(5-pentylpyrimidyl)-benzoate
trans-4-butylcyclohexyl p-(5-pentylpyrimidyl)-benzoate
trans-4-pentylcyclohexyl p-(5-pentylpyrimidyl)-benzoate
trans-4-heptylcyclohexyl p-(5-pentylpyrimidyl)-benzoate
trans-4-cyanocyclohexyl p-(5-pentylpyrimidyl)-benzoate
trans-4-ethoxycyclohexyl p-(5-pentylpyrimidyl)-benzoate
trans-4-butoxycyclohexyl p-(5-pentylpyrimidyl)-benzoate
trans-4-hexoxycyclohexyl p-(5-pentylpryimidyl)-benzoate
trans-4-ethylcyclohexyl p-(5-heptylpyrimidyl)-benzoate
trans-4-propylcyclohexyl p-(5-heptylpyrimidyl)-bepzoate
trans-4-butylcyclohexyl p-(5-heptylpyrimidyl)-benzoate
trans-4-pentylcyclohexyl p-(5-heptylpyrimidyl)-benzoate
trans-4-heptylcyclohexyl p-(5-heptylpyrimidyl)-benzoate
trans-4-cyanocyclohexyl p-(5-heptylpyrimidyl)-benzoate
trans-4-ethoxycyclohexyl p-(5-heptylpyrimidyl)-benzoate
trans-4-butoxycyclohexyl p-(5-heptylpyrimidyl)-benzoate trans-4-hexoxycyclohexyl p-(5-heptylpyrimidyl)-benzoate

EXAMPLE 2

A mixture of 1.3 g of (5-n-propylpyrimidyl)benzoic chloride, 25 ml of pyridine and 0.5 g of n-pentanol is stirred at 60° for 2 hours and, after cooling down, is worked up as customary. This gives n-pentyl p-(5-n-propylpyrimidyl)-benzoate.

EXAMPLE 3

A mixture of 40 g of 5-n-nonyl-2-(4-carbomethoxyphenyl)-4,6-dichloropyrimidine (obtainable by condensing 4-carbomethoxybenzamidine hydrochloride with ethyl n-nonylmalonate and subsequently reacting the 4,6-dihydroxy compound with phosphorus oxychloride) and 40 ml of triethylamine is dissolved in 400 ml of methanol and, after addition of 20 g of 5 percent palladium carbon, hydrogenated under atmospheric pressure at 50° until the calculated amount of hydrogen has been taken up. Working up gives methyl p-(5-nonylpyrimidyl)-benzoate, m.p. 61.7°, c.p. 65°.

Prepared analogously:
methyl p-(5-propylpyrimidyl)-benzoate
ethyl p-(5-propylpyrimidyl)-benzoate
propyl p-(5-propylpyrimidyl)-benzoate
butyl p-(5-propylpyrimidyl)-benzoate
pentyl p-(5-propylpyrimidyl)-benzoate
hexyl p-(5-propylpyrimidyl)-benzoate
heptyl p-(5-propylpyrimidyl)-benzoate
octyl p-(5-propylpyrimidyl)-benzoate
nonyl p-(5-propylpyrimidyl)-benzoate
decyl p-(5-propylpyrimidyl)-benzoate
methyl p-(5-ethylpyrimidyl)-benzoate
ethyl p-(5-ethylpyrimidyl)-benzoate
propyl p-(5-ethylpyrimidyl)-benzoate
butyl p-(5-ethylpyrimidyl)-benzoate
pentyl p-(5-ethylpyrimidyl)-benzoate
hexyl p-(5-ethylpyrimidyl)-benzoate
heptyl p-(5-ethylpyrimidyl)-benzoate
octyl p-(5-ethylpyrimidyl)-benzoate
nonyl p-(5-ethylpyrimidyl)-benzoate
decyl p-(5-ethylpyrimidyl)-benzoate
methyl p-(5-butylpyrimidyl)-benzoate
ethyl p-(5-butylpyrimidyl)-benzoate
propyl p-(5-butylpyrimidyl)-benzoate
butyl p-(5-butylpyrimidyl)-benzoate
pentyl p-(5-butylpyrimidyl)-benzoate
hexyl p-(5-butylpyrimidyl)-benzoate
heptyl p-(5-butylpyrimidyl)-benzoate
octyl p-(5-butylpyrimidyl)-benzoate
nonyl p-(5-butylpyrimidyl)-benzoate
decyl p-(5-butylpyrimidyl)-benzoate
methyl p-(5-pentylpyrimidyl)-benzoate
ethyl p-(5-pentylpyrimidyl)-benzoate
propyl p-(5-pentylpyrimidyl)-benzoate
butyl p-(5-pentylpyrimidyl)-benzoate
pentyl p-(5-pentylpyrimidyl)-benzoate
hexyl p-(5-pentylpyrimidyl)-benzoate
heptyl p-(5-pentylpyrimidyl)-benzoate
octyl p-(5-pentylpyrimidyl)-benzoate
nonyl p-(5-pentylpyrimidyl)-benzoate
decyl p-(5-pentylpyrimidyl)-benzoate
methyl p-(5-hexylpyrimidyl)-benzoate
ethyl p-(5-hexylpyrimidyl)-benzoate
propyl p-(5-hexylpyrimidyl)-benzoate
butyl p-(5-hexylpyrimidyl)-benzoate
pentyl p-(5-hexylpyrimidyl)-benzoate
hexyl p-(5-hexylpyrimidyl)-benzoate
heptyl p-(5-hexylpyrimidyl)-benzoate
octyl p-(5-hexylpyrimidyl)-benzoate
nonyl p-(5-hexylpyrimidyl)-benzoate
decyl p-(5-hexylpyrimidyl)-benzoate
methyl p-(5-heptylpyrimidyl)-benzoate
ethyl p-(5-heptylpyrimidyl)-benzoate, m.p. 85°
propyl p-(5-heptylpyrimidyl)-benzoate, m.p. 63.7°, c.p. 66.8°
butyl p-(5-heptylpyrimidyl)-benzoate, m.p. 60°, c.p. 56°
pentyl p-(5-heptylpyrimidyl)-benzoate, m.p. 55.3°, c.p. 55.7°
hexyl p-(5-heptylpyrimidyl)-benzoate, m.p. 52.0°, c.p. 52.4°
heptyl p-(5-heptylpyrimidyl)-benzoate, m.p. 52.3°, c.p. 51.2°
octyl p-(5-heptylpyrimidyl)-benzoate, m.p. 53.8°, c.p. 49.1°
nonyl p-(5-heptylpyrimidyl)-benzoate
decyl p-(5-heptylpyrimidyl)-benzoate
ethyl p-(5-nonylpyrimidyl)-benzoate, m.p. 62°, c.p. 65°, $\Delta\epsilon = +4.3$
propyl p-(5-nonylpyrimidyl)-benzoate
butyl p-(5-nonylpyrimidyl)-benzoate
pentyl p-(5-nonylpyrimidyl)-benzoate, m.p. 55°, c.p. 57°
hexyl p-(5-nonylpyrimidyl)-benzoate
heptyl p-(5-nonylpyrimidyl)-benzoate
octyl p-(5-nonylpyrimidyl)-benzoate
nonyl p-(5-nonylpyrimidyl)-benzoate
decyl p-(5-nonylpyrimidyl)-benzoate
methyl p-(5-decylpyrimidyl)-benzoate
ethyl p-(5-decylpyrimidyl)-benzoate
propyl p-(5-decylpyrimidyl)-benzoate
butyl p-(5-decylpyrimidyl)-benzoate
pentyl p-(5-decylpyrimidyl)-benzoate
heptyl p-(5-decylpyrimidyl)-benzoate

EXAMPLE 4

A mixture of 25.6 g of 2-(4-hydroxyphenyl)-5-n-hexylpyrimidine, 17.5 g of ethyl bromoacetate and 14.5 g of potassium carbonate is heated with stirring at 100° in 75 ml of dimethylformamide for 12 hours. The salt is filtered off with suction, the residue is concentrated by evaporation and taken up in ether and washed with water until neutral. Customary working up gives ethyl 4-(5-n-hexylpyrimidin-2-yl)-phenoxy acetate.

Prepared analogously:
ethyl 4-(5-heptylpyrimidin-2-yl)-phenoxy acetate
ethyl 4-(5-octylpyrimidin-2-yl)-phenoxy acetate
ethyl 4-(5-nonylpyrimidin-2-yl)-phenoxy acetate
ethyl 4-(5-decylpyrimidin-2-yl)-phenoxy acetate
propyl 4-(5-propylpyrimidin-2-yl)-phenoxy acetate
propyl 4-(5-butylpyrimidin-2-yl)-phenoxy acetate
propyl 4-(5-propylpyrimidin-2-yl)-phenoxy acetate
propyl 4-(5-hexylpyrimidin-2-yl)-phenoxy acetate
propyl 4-(5-heptylpyrimidin-2-yl)-phenoxy acetate
propyl 4-(5-nonylpyrimidin-2-yl)-phenoxy acetate

EXAMPLE 5

The method of Example 4 is used to convert 2-(4-hydroxyphenyl)-5-n-octylpyrimidine and the methanesulfonate of ethylene glycol monoethyl ether into 2-[4-(3-oxa-pentyl)-oxyphenyl]-5-n-octylpyrimidine.

Prepared analogously:
2-[4-(3-oxapentyl)-oxy-phenyl]-5-propylpyrimidine
2-[4-(3-oxapentyl)-oxy-phenyl]-5-butylpyrimidine
2-[4-(3-oxapentyl)-oxy-phenyl]-5-pentylpyrimidine 2-[4-(3-oxapentyl)-oxy-phenyl]-5-hexylpyrimidine
2-[4-(3-oxapentyl)-oxy-phenyl]-5-heptylpyrimidine
2-[4-(3-oxapentyl)-oxy-phenyl]-5-nonylpyrimidine
2-[4-(3-oxapentyl)-oxy-phenyl]-5-decylpyrimidine
2-[4-(2-oxapentyl)-oxy-phenyl]-5-propylpyrimidine
2-[4-(2-oxapentyl)-oxy-phenyl]-5-butylpyrimidine
2-[4-(2-oxapentyl)-oxy-phenyl]-5-pentylpyrimidine
2-[4-(2-oxapentyl)-oxy-phenyl]-5-hexylpyrimidine
2-[4-(2-oxapentyl)-oxy-phenyl]-5-heptylpyrimidine
2-[4-(2-oxapentyl)-oxy-phenyl]-5-nonylpyrimidine
2-[4-(3-oxahexyl)-oxy-phenyl]-5-propylpyrimidine
2-[4-(3-oxahexyl)-oxy-phenyl]-5-butylpryimidine
2-[4-(3-oxahexyl)-oxy-phenyl]-5-pentylpyrimidine
2-[4-(3-oxahexyl)-oxy-phenyl]-5-hexylpyrimidine
2-[4-(3-oxahexyl)-oxy-phenyl]-5-heptylpyrimidine
2-[4-(3-oxahexyl)-oxy-phenyl]-5-nonylpyrimidine
2-[4-(3-oxahexyl)-oxy-phenyl]-5-decylpyrimidine
2-[4-(3-oxabutyl)-oxy-phenyl]-5-propylpyrimidine
2-[4-(3-oxabutyl)-oxy-phenyl]-5-butylpyrimidine
2-[4-(3-oxabutyl)-oxy-phenyl]-5-pentylpyrimidine
2-[4-(3-oxabutyl)-oxy-phenyl]-5-hexylpyrimidine
2-[4-(3-oxabutyl)-oxy-phenyl]-5-heptylpyrimidine
2-[4-(3-oxabutyl)-oxy-phenyl]-5-nonylpyrimidine
2-[4-(3-oxabutyl)-oxy-phenyl]-5-decylpyrimidine

EXAMPLE 6

6.5 g of heptylmalondialdehyde tetraethyl acetal, 5.2 g of 4-n-hexylmercaptobenzamidine hydrochloride and 10 ml of dimethylformamide is heated at 150° for 12 hours. The reaction mixture is then taken up in dichloromethane, washed with sodium hydrogencarbonate solution and water until neutral, and dried, and the solvent is filtered off. This gives 2-(4-n-hexylmer-captophenyl)-5-n-heptylpyrimidine.

Prepared analogously:
2-(4-hexylmercaptophenyl)-5-propylpyrimidine
2-(4-hexylmercaptophenyl)-5-butylpyrimidine
2-(4-hexylmercaptophenyl)-5-pentylpyrimidine
2-(4-hexylmercaptophenyl)-5-octylpyrimidine
2-(4-hexylmercaptophenyl)-5-nonylpyrimidine
2-(4-hexylmercaptophenyl)-5-decylpyrimidine
2-(4-methylmercaptophenyl)-5-propylpyrimidine
2-(4-methylmercaptophenyl)-5-butylpyrimidine
2-(4-methylmercaptophenyl)-5-pentylpyrimidine
2-(4-methylmercaptophenyl)-5-heptylpyrimidine, m.p. 52°
2-(4-methylmercaptophenyl)-5-octylpyrimidine
2-(4-methylmercaptophenyl)-5-nonylpyrimidine
2-(4-methylmercaptophenyl)-5-decylpyrimidine
2-(4-butylmercaptophenyl)-5-propylpyrimidine
2-(4-butylmercaptophenyl)-5-butylpyrimidine
2-(4-butylmercaptophenyl)-5-pentylpyrimidine
2-(4-butylmercaptophenyl)-5-heptylpyrimidine
2-(4-butylmercaptophenyl)-5-octylpyrimidine
2-(4-butylmercaptophenyl)-5-nonylpyrimidine
2-(4-butylmercaptophenyl)-5-decylpyrimidine
2-(4-pentylmercaptophenyl)-5-propylpyrimidine
2-(4-pentylmercaptophenyl)-5-butylpyrimidine
2-(4-pentylmercaptophenyl)-5-pentylpyrimidine
2-(4-pentylmercaptophenyl)-5-heptylpyrimidine, m.p. 52.8°
2-(4-pentylmercaptophenyl)-5-octylpyrimidine
2-(4-pentylmercaptophenyl)-5-nonylpyrimidine
2-(4-pentylmercaptophenyl)-5-decylpyrimidine
2-(4-heptylmercaptophenyl)-5-propylpyrimidine
2-(4-heptylmercaptophenyl)-5-butylpyrimidine
2-(4-heptylmercaptophenyl)-5-pentylpyrimidine
2-(4-heptylmercaptophenyl)-5-heptylpyrimidine
2-(4-heptylmercaptophenyl)-5-octylpyrimidine
2-(4-heptylmercaptophenyl)-5-nonylpyrimidine
2-(4-heptylmercaptophenyl)-5-decylpyrimidine
2-(4-octylmercaptophenyl)-5-propylpyrimidine
2-(4-octylmercaptophenyl)-5-butylpyrimidine
2-(4-octylmercaptophenyl)-5-pentylpyrimidine
2-(4-octylmercaptophenyl)-5-heptylpyrimidine, m.p. 43°, c.p. 44°
2-(4-octylmercaptophenyl)-5-octylpyrimidine
2-(4-octylmercaptophenyl)-5-nonylpyrimidine
2-(4-octylmercaptophenyl)-5-decylpyrimidine
2-(4-nonylmercaptophenyl)-5-propylpyrimidine
2-(4-nonylmercaptophenyl)-5-butylpyrimidine
2-(4-nonylmercaptophenyl)-5-pentylpyrimidine
2-(4-nonylmercaptophenyl)-5-heptylpyrimidine
2-(4-nonylmercaptophenyl)-5-octylpyrimidine
2-(4-nonylmercaptophenyl)-5-nonylpyrimidine
2-(4-nonylmercaptophenyl)-5-decylpyrimidine
2-(4-decylmercaptophenyl)-5-propylpyrimidine
2-(4-decylmercaptophenyl)-5-butylpyrimidine
2-(4-decylmercaptophenyl)-5-pentylpyrimidine
2-(4-decylmercaptophenyl)-5-heptylpyrimidine
2-(4-decylmercaptophenyl)-5-octylpyrimidine
2-(4-decylmercaptophenyl)-5-nonylpyrimidine
2-(4-decylmercaptophenyl)-5-decylpyrimidine

EXAMPLE 7

A mixture of 5.4 g of 2-(4-hydroxyphenyl)-5-n-heptylpyrimidine, 23 g of 1,5-dibromopentane and 3 g of potassium carbonate is heated with stirring at 100° in 50 ml of DMF for 12 hours. Customary working up gives 2-[4-(5-bromopentyl)-oxyphenyl]-5-n-heptylpyrimidine.

Prepared analogously:
2-[4-(5-bromopentyl)-oxyphenyl]-5-propylpyrimidine
2-[4-(5-bromopentyl)-oxyphenyl]-5-butylpyrimidine
2-[4-(5-bromopentyl)-oxyphenyl]-5-pentylpyrimidine
2-[4-(5-bromopentyl)-oxyphenyl]-5-hexylpyrimidine
2-[4-(5-bromopentyl)-oxyphenyl]-5-nonylpyrimidine

EXAMPLE 8

Ammonia is passed with stirring and cooling into a mixture of 2.55 g of 2-(4-aminophenyl)-5-n-hexylpyrimidine (obtainable from 4-(5-n-hexylpyrimidin-2-yl)-benzamide by Hofmann degradation) and 10 ml of toluene. After 10 min., 0.8 g of hydrogen sulfide is added dropwise. The introduction of ammonia is discontinued once no more gas is absorbed. Air is sucked through for 5 min., then 6 ml of 20 percent phosgene solution in toluene are added dropwise, which is followed by 30 min. of stirring. The precipitated ammonium chloride is filtered off with suction, and the toluene solution is concentrated down by evaporation to a residue which is recrystallized. This gives 4-(5-n-hexylpyrimidin-2-yl)-phenyl isothiocyanate.

Prepared analogously:
4-(5-ethylpyrimidin-2-yl)-phenyl isothiocyanate
4-(5-propylpyrimidin-2-yl)-phenyl isothiocyanate, m.p. 114°
4-(5-butylpyrimidin-2-yl)-phenyl isothiocyanate
4-(5-pentylpyrimidin-2-yl)-phenyl isothiocyanate, m.p. 47°, c.p. 86°
4-(5-heptylpyrimidin-2-yl)-phenyl isothiocyanate, m.p. 46°, c.p. 89°, $\Delta\epsilon = 21.9$
4-(5-octylpyrimidin-2-yl)-phenyl isothiocyanate
4-(5-nonylpyrimidin-2-yl)-phenyl isothiocyanate
4-(5-decylpyrimidin-2-yl)-phenyl isothiocyanate The examples below relate to liquid-crystalline phases according to the invention:

EXAMPLE A

A liquid-crystalline phase composed of
8% of 2-p-cyanophenyl-5-butyl-1,3-dioxane,
7% of 2-p-cyanophenyl-5-pentyl-1,3-dioxane,
8% of 4-cyano-4'-(trans-4-pentylcyclohexyl)-biphenyl,
5% of 4-ethyl-4'-(trans-4-pentylcyclohexyl)-biphenyl,
10% of trans-4-pentylcyclohexyl p-(5-propylpyrimidyl)-benzoate,
5% of 2-p-hexoxyphenyl-5-hexylpyrimidine,
6% of 2-p-heptoxyphenyl-5-hexylpyrimidine,
8% of 2-p-nonoxyphenyl-5-hexylpyrimidfne,
8% of 2-p-undecoxyphenyl-5-hexylpyrimidine,
7% of p-methoxyphenyl trans-4-propylcyclohexanecarboxylate,
7% of p-ethoxyphenyl trans-4-propylcyclohexanecarboxylate,
7% of p-methoxyphenyl trans-4-butylcyclohexanecarboxylate,
7% of p-ethoxyphenyl trans-4-butylcyclohexanecarboxylate and
7% of p-methoxyphenyl trans-4-pentylcyclohexanecarboxylate has a viscosity of $49 \times 10^{-3}$ Pa.s and is highly suitable for highly multiplexible liquid crystal display elements.

EXAMPLE B

A liquid-crystalline phase composed of
8.0% of trans-1-p-propylphenyl-4-pentylcyclohexane,
7.0% of 2-p-cyanophenyl-5-propyl-1,3dioxane,
8.0% of 2-p-cyanophenyl-5-butyl-1,3dioxane,
7.0% of 2-p-cyanophenyl-5-pentyl-1,3-dioxane,
7.5% of 4-cyano-4'-(trans-4-pentylcyclohexyl)-biphenyl,
5.0% of 4-ethyl-4'-(trans-4-pentylcyclohexyl)-biphenyl,
5.0% of 4-ethyl-4'-(trans-4-propylcyclohexyl)-biphenyl,
5.0% of 2-p-pentoxyphenyl-5-hexylpyrimidine,
5.0% of 2-p-hexoxyphenyl-5-hexylpyrimidine,
6.0% of 2-p-heptoxyphenyl-5-hexylpyrimidine,
8.0% of 2-p-nonoxyphenyl-5-hexylpyrimidine,
8.0% of 2-p-undecoxyphenyl-5-hexylpyrimidine,
0.5% of pentyl p-(5-propylpyrimidyl)-benzoate,
7.0% of p-methoxyphenyl trans-4-propylcyclohexanecarboxylate,
7.0% of p-ethoxyphenyl trans-4-propylcyclohexanecarboxylate and
6.0% of p-methoxyphenyl trans-4-butylcyclohexanecarboxylate has a clear point of 64°, a viscosity of $45 \times 10^{-3}$ Pa.s and is highly suitable for highly multiplexible liquid crystal display elements.

EXAMPLE C p A liquid-crystalline phase composed of

7% of 2-p-cyanophenyl-5-propyl-1,3-dioxane,
6% of 2-p-cyanophenyl-5-butyl-1,3-dioxane,
5% of 2-p-cyanophenyl-5-pentyl-1,3-dioxane,
4% of 2-p-pentoxyphenyl-5-hexylpyrimidine,
4% of 2-p-hexoxyphenyl-5-hexylpyrimidine,
5% of 2-p-heptoxyphenyl-5-hexylpyrimidine,
7% of 2-p-nonoxyphenyl-5-hexylpyrimidine,
7% of 2-p-undecoxyphenyl-5-hexylpyrimidine,
6% of p-methoxyphenyl trans-4-propylcyclohexanecarboxylate,
4% of p-methoxyphenyl trans-4-butylcyclohexanecarboxylate,
3% of p-methoxyphenyl trans-4-pentylcyclohexanecarboxylate,
9% of trans-1-p-propylphenyl-4-pentylcyclohexane,
3% of p-trans-4-propylcyclohexylphenyl butyrate,
18% of trans-4-pentylcyclohexyl p-(5-propylpyrimidyl)-benzoate,
9% of trans-4-propylcyclohexyl p-(5-propylpyrimidyl)-benzoate,
3% of trans-4-propylcyclohyexyl p-(5-pentylpyrimidyl)-benzoate is highly suitable for highly multiplexible liquid crystal display elements.

EXAMPLE D

A liquid-crystalline phase consisting of
5% of 2-p-cyanophenyl-5-ethyl-1,3-dioxane,
7% of 2-p-cyanophenyl-5-propyl-1,3-dioxane,
8% of 2-p-cyanophenyl-5-butyl-1,3-dioxane,
7% of 2-p-cyanophenyl-5-pentyl-1,3-dioxane,
6% of 4-(trans-4-pentylcyclohexyl)-4'-(trans-4-propylcyclohexyl)-2-fluorobiphenyl,
5% of 4,4'-bis-(trans-4-pentylcyclohexyl)-biphenyl,
6% of 4,4'-bis-(trans-4-pentylcyclohexyl)-2-fluorobiphenyl,
5% of 2-p-hexyloxy-5-hexylpyrimidine,
6% of 2-p-heptyloxy-5-hexylpyrimidine,
5% of 2-p-nonyloxy-5-hexylpyrimidine,
6% of 2-p-heptyloxy-5-heptylpyrimidine,
5% of 2-p-nonyloxy-5-heptylpyrimidine,
11% of trans-1-p-methoxyphenyl-4-propylcyclohexane,
5% of methyl p-(5-nonylpyrimidyl)-benzoate,
2% of ethyl p-(5-nonylpyrimidyl)-benzoate and
11% of trans-1-p-propylphenyl-4-pentylcyclohexane has a melting point of $-11°$, a clear point of 61° and a $K_3/K_1$ of 0.82 at 20°.

EXAMPLE E

A liquid-crystalline phase consisting of
7% 35 7% of 2-p-cyanophenyl-5-pentylpyrimidine,
8% of 4-(5-heptylpyrimidin-2-yl)-phenyl isothiocyanate,
8% of 2-p-cyanophenyl-5-p-butylphenylpyrimidine,
5% of 4-ethyl-4'-(trans-4-propylcyclohexyl)-biphenyl,
5% of 4-ethyl-4'-(trans-4-pentylcyclohexyl)-biphenyl,
7% of 2-p-methoxyphenyl-5-hexylpyrimidine,
6% of 2-p-nonyloxyphenyl-5-heptylpyrimidine,
7% of 2-p-methoxyphenyl-5-nonylpyrimidine,
6% of 2-p-hexyloxyphenyl-5-nonylpyrimidine,
6% of 2-p-nonyloxyphenyl-5-nonylpyrimidine,
7% of p-methoxyphenyl trans-4-propylcyclohexanecarboxylate,
7% of p-ethoxyphenyl trans-4-propylcyclohexanecarboxylate,
7% of p-methoxyphenyl trans-4-butylcyclohexanecarboxylate,
7% of p-ethoxyphenyl trans-4-butylcyclohexanecarboxylate and
7% of p-methoxyphenyl trans-4-pentylcyclohexanecarboxylate has a clear point of 70°, up to $-20°$ no smectic phase, $\Delta\epsilon = +7.1$, $\Delta n = 0.1654$ and $K_3/K_1 = 0,71$ at 20°.

We claim:

1. A pyrimidine of the formula

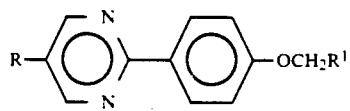

in which R is a straight chain alkoxy group of 1-15 C atoms, and $R^1$ is an alkyl group of 2 to 12 C atoms in which one $CH_2$ group is replaced by —CHY—, Y being halogen or CN.

2. A liquid crystalline phase having at least two liquid crystalline components, wherein at least one component is a compound of claim 1.

3. In a liquid crystalline display element comprising a liquid crystalline phase, the improvement wherein the phase is one of claim 2.

4. A compound of claim 1, wherein Y is halogen.

5. A liquid crystalline phase having at least two liquid crystalline components, wherein at least one component is a compound of claim 4.

6. In a liquid crystalline display element comprising a liquid crystalline phase, the improvement wherein the phase is one of claim 5.

7. A compound of claim 1, wherein the number of carbon atoms is $R^1$ is 5-12.

* * * * *